United States Patent [19]

Stapp

[11] 4,113,971

[45] Sep. 12, 1978

[54] PROCESS FOR PREPARING DIACYLOXY OLEFINS

[75] Inventor: Paul R. Stapp, Bartlesville, Okla.

[73] Assignee: Phillips Petroleum Company, Bartlesville, Okla.

[21] Appl. No.: 551,834

[22] Filed: Feb. 21, 1975

[51] Int. Cl.$^2$ ............................................. C07C 67/05
[52] U.S. Cl. .................... 560/246; 260/410.6; 260/465 D; 260/465.4; 560/1; 560/89; 560/112; 560/127; 560/198; 560/230; 252/441
[58] Field of Search ........... 260/497 R, 476 R, 468 R, 260/410.6, 465 D, 465.4; 560/246, 1, 89, 112, 127, 198, 230

[56] References Cited

U.S. PATENT DOCUMENTS

| | | | |
|---|---|---|---|
| 2,174,985 | 10/1939 | Lazier | 260/497 R |
| 2,702,232 | 2/1955 | Arnold et al. | 260/497 R |
| 2,900,396 | 10/1957 | Harrison | 260/346.1 |
| 3,299,110 | 1/1967 | Pine | 260/497 R |
| 3,335,174 | 8/1967 | Norton | 260/497 R |
| 3,644,497 | 2/1972 | Mesich | 260/497 R |
| 3,671,577 | 6/1972 | Ono et al. | 260/497 R |

FOREIGN PATENT DOCUMENTS 1,138,366 1/1969 United Kingdom.
1,170,222 11/1969 United Kingdom.

Primary Examiner—James O. Thomas, Jr.
Assistant Examiner—Michael Shippen

[57] ABSTRACT

Diacyloxy olefins are prepared by the reaction of a conjugated diolefin with a carboxylic acid in the presence of free oxygen and a Group VIB metal oxide.

7 Claims, No Drawings

PROCESS FOR PREPARING DIACYLOXY OLEFINS

This invention relates to a process for the production of unsaturated diesters.

Various methods for the production of unsaturated diesters are known in the art.

It is an object of this invention to provide a novel process for the production of unsaturated diesters.

Other objects, aspects and advantages of this invention will be readily apparent to those skilled in the art from the reading of the following disclosure.

In accordance with the present invention there is provided a process for the production of unsaturated diesters which comprises reacting a conjugated diolefin with a carboxylic acid in the presence of free oxygen and a Group VIB metal oxide.

The conjugated diolefin is selected from the group consisting of acyclic conjugated diolefins having from 4 to 16 carbon atoms per molecule and corresponding to the general formula

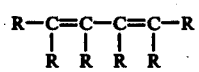

and cyclic conjugated diolefins having from 5 to 16 carbon atoms per molecule and corresponding to the general formula

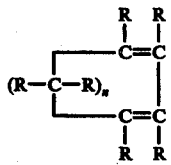

wherein, in each of the above formulas, R can be hydrogen, halogen, cyano, —COOR′ or a hydrocarbyl containing up to 12 carbon atoms selected from the group consisting of alkyl, aryl, cycloalkyl and combinations thereof, such as aralkyl, alkaryl cycloalkyl and the like. R′ can be hydrogen, alkyl of up to 10 carbon atoms or aryl of up to 10 carbon atoms. The integer $n$ can range from 1 to 12.

Examples of suitable conjugated diolefins include: 1,3-butadiene, 2-methyl-1,3-butadiene, 2-chloro-1,3-butadiene, 2-ethyl-1,3-butadiene, 2-chloro-3-methyl-1,3-butadiene, 1,4-diphenyl-1,3-butadiene, 1,3-hexadiene, 1,3-pentadiene, 1,3-octadiene, 1,3-cyclohexadiene, 1,3-cyclooctadiene, 1,3-cyclododecadiene, 2-cyano-1,3-butadiene, 5-methyl-1,3-cyclohexadiene, 2,4-cyclohexadiene-1,2-dicarboxylic acid, octafluoro-1,3-cyclohexadiene, hexachloropentadiene, 5,6,7,8-tetrabromo-1,3-cyclooctadiene, 2-cyclohexyl-1,3-butadiene, 2-methylene-3-butenoic acid, 2,4-pentadienenitrile, cyclopentadiene, 2-carbethoxy-1,3-butadiene, and the like.

In a presently preferred embodiment the conjugated diolefins employed in the process of this invention are those which contain only carbon and hydrogen.

The carboxylic acid is selected from the group consisting of monocarboxylic acids having from 2 to 18 carbon atoms per molecule characterized by the general formula

R″—COOH and dicarboxylic acids having from 2 to 18 carbon atoms per molecule characterized by the formula

R‴(COOH)$_2$, wherein R″ is selected from the group consisting of alkyl, cycloalkyl and aryl groups and halogen, cyano and —COOR′ substituted derivatives thereof, wherein up to four halogen, cyano or —COOR′ substituents can be present in the R″ group; and wherein R‴ is selected from the group consisting of a valence bond and alkylene, cycloalkylene and arylene groups and halogen, cyano and —COOR′ substituted derivatives thereof, wherein up to four halogen, cyano or —COOR′ substituents can be present in the R‴ group. R′ has been previously defined.

Examples of suitable carboxylic acids include: acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyanobenzoic acid, 2,3,4,5-tetrachlorobenzoic acid, ethyl hydrogen-o-phthalate, and the like.

The reaction according to this invention is carried out by the catalytic action of at least one Group VIB metal oxide. Examples of suitable metal oxides for use as catalyst in the present invention include: CrO, CrO$_2$, Cr$_2$O$_3$, CrO$_3$, MoO$_2$, Mo$_2$O$_3$, MoO$_3$, Mo$_2$O$_5$, WO$_2$, W$_2$O$_5$, W$_4$O$_{11}$, WO$_3$, and the like and mixtures thereof. If desired, the Group VIB metal oxide catalyst can be dispersed in or supported on an inert support material such as silica, alumina, silica-alumina, diatomaceous earth, clays and the like.

The amount of Group VIB metal oxide catalyst employed in the process of this invention is in the range of from about 0.1 to about 20 mole percent based upon the conjugated diolefin employed. It is presently preferred that the catalyst be present in the reaction mixture in an amount ranging from about 1 to about 15 mole percent.

It is optional, though presently preferred, to include in the reaction mixture an alkali metal salt as catalyst adjuvant. Suitable compounds of the alkali metals include the halides, carboxylates and oxides. Of the alkali metal salts, the lithium salts are especially preferred. When used, the alkali metal salt adjuvant is present in an amount ranging from 0.1 to 2.0 molar, preferably from about 0.7 to about 1.5 molar, based upon the carboxylic acid present as diluent and reactant.

Examples of suitable alkali metal salts which can be employed as catalyst adjuvants include: lithium chloride, lithium bromide, lithium iodide, lithium acetate, lithium benzoate, lithium oxide, lithium octadecanoate, sodium chloride, sodium bromide, sodium acetate, potassium chloride, potassium acetate, potassium benzoate, rubidium chloride, rubidium bromide, rubidium acetate, cesium chloride, cesium acetate, cesium oxide and the like and mixtures thereof.

It is optional to employ a dihalobutene, such as 1,4-dichloro-2-butene or the corresponding dibromo compound, as a second catalyst adjuvant. When used, the dihalobutene is present in the reaction mixture in an amount ranging from 0.1 to 10 moles per mole of Group VIB metal oxide, preferably from 0.5 to 5 moles per mole of metal oxide.

The reaction of the instant invention is an oxidation reaction and as such is carried out in the presence of free oxygen. The amount of oxygen present is not believed to be critical though it is recognized that an undesirably slow reaction will result if the concentration of oxygen is very low. Essentially pure oxygen can be employed as well as mixtures of oxygen with inert gases or air can be employed as a source of free oxygen for the instant reaction. It is recognized that explosive conditions could be obtained if the amount of oxygen added to the reaction system is not under control. The reaction of this invention, as is true with many oxidation reactions, appears to be highly exothermic and this too indicates caution in adding oxygen to the system. Because of these considerations it is desirable to add the oxygen incrementally or continuously during the reaction to avoid the explosive range of oxygen concentration and to allow better control of the temperature of the reaction. A reaction vessel with efficient mixing means is also desirable to avoid build-up of dangerous concentrations of free oxygen.

The reaction of this invention is carried out at a temperature in the range of 30° C. to about 200° C., preferably from about 100° to about 150° C.

The reaction is carried out at a pressure of from 0.1 to 1000, preferably from 5 to 200 psig, of oxygen above autogenous pressure at the temperature employed.

The reaction time ranges from 0.1 to about 12 hours. The reaction time depends upon the temperature, catalyst activity and the oxygen pressure employed.

As described above, the reaction of the instant invention is carried out in the presence of a carboxylic acid which provides the acyl moiety of the final product. It is optional, though presently preferred, to employ, as part of the reaction mixture, the corresponding carboxylic acid anhydride in addition to the carboxylic acid. The use of a carboxylic anhydride serves to simplify the purification and separation steps by reducing the amount of by-products which contain free hydroxy groups.

The process of this invention can be carried out in a batch or a continuous fashion.

The process of this invention can be carried out in the liquid phase or in the gas phase.

In a presently preferred embodiment of this invention, the process of this invention is carried out in the liquid phase.

When conducted in the liquid phase, it is preferred that the carboxylic acid employed in the process of this invention be normally liquid or at least liquid under the conditions employed for the reaction. The presently preferred carboxylic acid is acetic acid.

Reaction mixtures obtained according to the process of this invention are generally vented to remove any unreacted oxygen and conjugated diolefin and then distilled to remove the carboxylic acid and anhydride, if present. The product remaining is usually distilled to recover one or more fractions containing the diacyloxy olefins. The catalyst can be recovered from the distillation residue and recycled to the reaction zone as desired. Any unreacted conjugated diolefin recovered from the reaction mixture can also be recycled to the reaction zone as desired. The diacloxy olefins which are recovered from the product mixture include in many instances an amount of 1,2- or vicinal- isomer which can be recycled to the reaction zone and thereby converted to the desired 1,4-diacyloxy olefin.

The above mentioned 1,4-diacyloxy olefins have utility as intermediates for the preparation of the corresponding saturated diols. For example, British Pat. No. 1,170,222 describes the ultimate preparation of tetrahydrofurans starting with conjugated diolefins and proceeding through the 1,4-diacyloxy butenes. Tetrahydrofuran itself, of course, would be produced starting with 1,3-butadiene.

The following examples illustrate the invention.

EXAMPLE I

A series of runs was conducted in a 250 ml Fisher-Porter aerosol compatibility bottle equipped with a magnetic stirrer. In each run, the reactor was charged with tungstic oxide ($WO_3$), 4.6 grams (22.5 mol) of 1,4-dibromo-2-butene (except Run 2), 75 mmol of a lithium salt, 50 ml of acetic acid, 25 ml of acetic anhydride and about 200 mmol of butadiene charged from the vapor phase. The reactor was pressured to 30 psig with oxygen, placed in an oil bath and heated to 140° C. About one hour was required to bring the temperature of the bath up to the desired temperature. During the course of the reaction period, the reactor was charged with additional oxygen intermittently by pressuring the reactor to about 120 psig with oxygen. At the end of the reaction period, the reactor was vented and the solids were removed by filtration. The filtrate was transferred to a distilling flask and fractionally distilled under reduced pressure into two or three fractions, which were analyzed by gas-liquid chromatography (GLC). The results obtained in this series of runs are presented below in Table I.

Table I

| Run No. | $WO_3$, mmol | Li Salt | Butadiene, mmol | Time, Hrs. | Diacetoxybutenes, mmol | | | |
|---|---|---|---|---|---|---|---|---|
| | | | | | 1,2- | 1,4- | Total | Yield[a] |
| 1 | 20 | -Br | 190.7 | 5 | 6.9 | 43.3 | 50.2 | 26 |
| 2[b] | 24 | -OAc . 2H$_2$O | 21.8 | 6 | 35.7 | 13.0 | 48.7 | 22 |
| 3 | 24 | -Br | 185.2 | 6 | —[c] | —[c] | 112 | 60 |

[a]Yield of diacetoxybutenes (total) based on butadiene charged.
[b]No 1,4-dibromo-2-butene present. Reaction mixture filtrate after acetate acid removal was extracted with ether, ether extract washed with water, neutralized with Na$_2$CO$_3$, dried over MgSO$_4$ and ether removed.
[c]Not determined.

The results of these runs demonstrate the effectiveness of tungstic oxide ($WO_3$) in catalyzing the conversion of 1,3-butadiene to diacetoxybutenes in the presence of oxygen and acetic acid.

EXAMPLE II

Another run was conducted according to the instant invention using the same apparatus as employed in the runs of Example I. In this run, the reactor was charged with 2.5 grams (20 mmol) of molybdenum dioxide ($MoO_2$), 6.5 grams (75 mmol) of lithium bromide, 4.6 grams (22.5 mmol) of 1,4-dibromo-2-butene, 50 ml of acetic acid, 25 ml of acetic anhydride and 10.9 grams (201.8 mmol) of butadiene from the vapor phase. The reactor was pressured to 30 psig with oxygen, placed in an oil bath and heated to 140° C. As in the runs of Example I, the reactor was pressured intermittently with oxygen to 120 psig. The reactor required about 30 minutes to reach the 140° C. reaction temperature after which the reaction was conducted for 4.75 hours. At the end of the reaction period, the reactor was vented and the solid materials separated by filtration. The filtrate was distilled to remove acetic acid. The distillation residue was then mixed with ether and water, and the layers were separated. The aqueous layer was extracted with ether, and the combined ether extracts were filtered, washed with water, neutralized with a sodium carbonate solution, and dried over magnesium sulfate. The ether solution was then filtered and the ether removed on a rotary evaporator. There remained 13.5 grams of a dark oil which was analyzed by gas-liquid phase chromatography. The analysis showed that there was obtained 9.3 mmol of 1,2-diacetoxy-3-butene and 31.8 mmol of 1,4-diacetoxy-2-butene for a diacetoxybutene yield of 20 percent based on the butadiene charged.

The results of this run demonstrate that molybdenum oxides are suitable catalysts for the process of the instant invention.

EXAMPLE III

Another run was conducted according to the process of this invention in the same apparatus as employed in the previous runs of Examples I and II. In this run, the reactor was charged with 2.3 grams (20 mmol) of chromium trioxide ($CrO_3$), 6.5 grams (75 mmol) of lithium bromide, 4.6 grams (22.5 mmol) of 1,4-dibromo-2-butene, 50 mol of acetic acid, 25 ml of acetic anhydride, and 10.8 grams (200 mmol) of butadiene from the vapor phase. The reactor was pressured to 30 psig with oxygen, placed in an oil bath and heated to 140° C. Again, as in the previous runs, the reactor was pressured with oxygen from time to time to about 120 psig. After about 45 minutes required to reach the reaction temperature, the reaction was conducted for 5.75 hours. At the end of the reaction period, the reactor was vented, and the reaction mixture transferred to a distilling flask. The mixture was distilled under reduced pressure to remove the acetic acid. The product fraction was analyzed by (GLC) as before and there was found 12.9 mmol of 1,2-diacetoxy-3-butene and 56.5 mmol of 1,4-diacetoxy-2-butene for a diacetoxybutene yield of 35 percent based on the butadiene charged.

The results of this run indicate that chromium oxides are suitable catalysts for the process of the instant invention.

EXAMPLE IV

Two runs were conducted employing the same apparatus as employed in the previous runs for the reaction of 1-hexene in the presence of oxygen, acetic acid and acetic anhydride with the catalysts of the instant invention.

The first of these two runs was carried out by charging the reactor with 2.3 grams (10 mmol) of tungstic oxide ($WO_3$), 6.5 grams (75 mmol) of lithium bromide, 50 ml of acetic acid, 25 ml of acetic anhydride, and 16.8 grams (200 mmol) of 1-hexene. The reactor was pressured to 30 psig with oxygen, placed in an oil bath and heated to 140° C. After about 1 hour to reach the reaction temperature, the reaction was conducted for an additional 5 hours with intermittent pressuring of the reactor with oxygen to about 120 psig. It was observed that very little oxygen uptake had occurred during the reaction period. Therefore, the reactor was vented and the reaction mixture was discarded since there was apparently little or no oxidation of the 1-hexene during the reaction period.

The second run was carried out by charging the reactor with 2.3 grams (10 mmol) of tungstic oxide ($WO_3$), 6.5 grams (75 mmol) of lithium bromide, 75 ml of sulfolane, 15 ml of water and 16 grams (200 mmol) of 1-hexene. The reactor was pressured to 30 psig with oxygen, placed in an oil bath and heated to 140° C. After about 30 minutes required to reach the reaction temperature, the reaction was conducted for an additional 4.75 hours with the intermittent addition of oxygen by pressuring the reactor to 120 psig with oxygen. As in the previous run employing 1-hexene, there was in this case also little oxygen uptake observed, thus indicating that the desired oxidation reaction of the 1-hexene had not taken place to any significant extent during the reaction period. The reactor contents were discarded.

The above results demonstrate that under the conditions employed a monoolefin reactant was essentially unreactive under reaction conditions suitable for use with conjugated diolefins in the process of the instant invention.

EXAMPLE V

Another run was conducted according to the process of this invention in the same apparatus employed in the previous runs. In this run, the reactor was charged with 5.0 grams of a finely ground tungstic oxide ($WO_3$) on silica catalyst (8 percent by weight $WO_3$, 1.7 mmol $WO_3$), 6.5 grams (75 mmol) lithium bromide, 4.6 grams (22.5 mmol) 1,4-dibromo-2-butene, 50 ml acetic acid, 25 ml acetic anhydride and 12.5 grams (231.5 mmol) butadiene from the vapor phase. The reactor was pressured to 30 psig with oxygen, placein in an oil bath and heated to 140° C. After about 45 minutes required to reach the reaction temperature, the reaction was conducted for 5 hours. At the end of the reaction period, the reactor was opened and the unreacted butadiene distilled into a Dry Ice/acetone cold trap which recovered 1.3 grams butadiene. The reaction mixture was filtered and the filtrate distilled under reduced pressure. The middle fraction of the three taken was found to contain 26.8 mmol of 3-buten-2-yl acetate, 9.7 mmol 1,2-diacetoxy-3-butene and 42.6 mmol 1,4-diacetoxy-2-butene for a diacetoxybutene yield of 22 percent based on the butadiene charged. Surprisingly, the yield of monoacetoxy butene was 27 percent based on the butadiene charged.

The results of this run demonstrate that tungsten oxide on an inert support such as silica is also operable for the oxidation of butadiene to diacetoxybutenes in the presence of acetic acid.

EXAMPLE VI

Another run was conducted according to the process of this invention in the same apparatus employed in the previous runs. The reactor was charged with 5.6 grams (24 mmol) of tungsten oxide ($WO_3$), 4.6 grams (22.5 mmol) of 1,4-dibromo-2-butene, 50 ml of acetic acid, 25 ml of acetic anhydride, and 11.8 grams (218 mmol) of butadiene charged from the vapor phase. The reactor was placed in an oil bath, pressured to 30 psig with oxygen and heated to 140° C. As in the previous runs, the reactor was pressured to 120 psig with oxygen intermittently. The reactor required about 1.25 hours to reach the 140° C. reaction temperature after which the reaction was continued for 6.3 hours. At the end of the reaction period, the reactor was vented and the contents filtered from solid material (3.6 grams) using a small amount of acetic anhydride as the wash liquid. The filtrate was distilled under reduced pressure through an 18 inches Vigreaux column. Two fractions were collected with the first fraction being essentially a mixture of acetic acid and acetic anhydride. The second fraction which weighed 12.3 grams was analyzed by gas-liquid phase chromatography, which revealed that there was obtained 5.4 grams (32 mmol) of 1,2-diacetoxy-3-butene, 0.7 grams (4 mmol) of cis-1,4-diacetoxy-2-butene and 1.5 grams (9 mmol) of trans-1,4-diacetoxy-2-butene for a total yield of 45 mmol of the diacetoxy butenes. This represents a 21 percent yield based on the amount of butadiene charged to the reactor. This result demonstrates that the catalyst system of the instant invention is operable in the absence of the alkali metal compound.

Reasonable variations and modifications, which will be apparent to those skilled in the art, can be made in this invention without departing from the spirit and scope thereof.

I claim:

1. A process for the production of unsaturated diesters which comprises reacting a conjugated diolefin with a carboxylic acid by contacting said diolefin and said acid with a catalytic amount of a catalyst consisting essentially of a Group VIB metal oxide or a Group VIB metal oxide and a catalyst adjuvant selected from the group consisting of alkali metal salts, dihalobutenes and mixtures thereof in the presence of free oxygen, wherein said conjugated diolefin is selected from the group consisting of acyclic conjugated diolefins having from 4 to 16 carbon atoms per molecule represented by the general formula

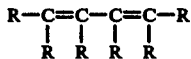

and cyclic conjugated diolefins having from 5 to 16 carbon atoms per molecule represented by the general formula

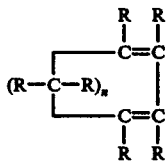

wherein, in each formula, each R is independently selected from the group consisting of hydrogen, halogen, cyano, —COOR', and alkyl, aryl and cycloalkyl radical groups and combinations thereof, of up to 12 carbon atoms per radical group, wherein R' is selected from the group consisting of hydrogen, alkyl of up to 10 carbon atoms and aryl of up to 10 carbon atoms; and wherein n is an integer having a value of 1 to 12 and wherein said carboxylic acid is selected from the group consisting of monocarboxylic acids having from 2 to 18 carbon atoms per molecule represented by the general formula

and dicarboxylic acids having from 2 to 18 carbon atoms per molecule represented by the general formula

wherein R" is selected from the group consisting of alkyl, cycloalkyl and aryl radical groups and halogen, cyano and —COOR' substituted derivatives thereof, wherein up to four of said halogen, cyano or —COOR' substituents can be present in said radical, wherein R' is selected from the group consisting of hydrogen, alkyl of up to 10 carbon atoms and aryl of up to 10 carbon atoms;

wherein R'" is selected drom the group consisting of a valence bond and alkylene, cycloalkylene and arylene radical groups and halogen, cyano and —COOR' substituted derivatives thereof wherein up to four of said halogen, cyano or —COOR' substituents can be present in said radical, wherein R' is as defined above; and wherein said salt is employed in an amount ranging from about 0.1 to about 2 molar based on said acid and said dihalobutene is employed in an amount ranging from about 0.1 to about 10 moles per mole of said metal oxide.

2. The process of claim 1 wherein said Group VIB metal oxide catalyst is present in an amount ranging from about 0.1 to about 20 mole percent based on the conjugated diene.

3. The process of claim 1 wherein said Group VIB metal oxide is supported on an inert support material.

4. The process of claim 1 wherein said reaction is carried out at a temperature in the range of 30° to about 200° C. at an oxygen pressure in the range of 0.1 to 1000 psig above autogenous pressure at the temperature employed.

5. The process of claim 1 wherein there is additionally present a carboxylic acid anhydride corresponding to the carboxylic acid employed.

6. The process of claim 1 wherein said conjugated diolefin is 1,3-butadiene, said carboxylic acid is acetic acid and said catalyst is tungstic oxide.

7. The process of claim 1 wherein said reaction is conducted in the liquid phase.

* * * * *